United States Patent [19]
Sherlock et al.

[11] Patent Number: 5,548,841
[45] Date of Patent: Aug. 27, 1996

[54] HEADBAND MAGNIFIER

[75] Inventors: Mary F. Sherlock; Marnie C. Averitt, both of Kerrville; Thomas W. Dowling, El Paso, all of Tex.

[73] Assignee: MFD Enterprises, Inc., Kerrville, Tex.

[21] Appl. No.: 279,548

[22] Filed: Jul. 25, 1994

Related U.S. Application Data

[63] Continuation-in-part of Ser. No. 14,845, Oct. 29, 1993, Pat. No. Des. 359,060.

[51] Int. Cl.$^6$ .................................................. A61F 9/00
[52] U.S. Cl. .............................. 2/15; 2/11; 2/418; 2/452; 2/DIG. 11; 351/155
[58] Field of Search ................................ 2/9, 10, 11, 12, 2/15, 171, 209.13, 417, 418, 422, 424, DIG. 11, 452; 351/155, 156; 359/815, 816

[56] References Cited

U.S. PATENT DOCUMENTS

| | | | |
|---|---|---|---|
| D. 194,284 | 12/1962 | Baratelli | D57/1 |
| D. 296,337 | 6/1988 | Caplan | D16/133 |
| D. 333,828 | 3/1993 | Baldassarre | D16/133 |
| D. 359,060 | 6/1995 | Sherlock et al. | D16/135 |
| 2,187,932 | 1/1940 | Cornell | 2/8 |
| 2,280,354 | 4/1942 | Rezos | 88/41 |
| 2,419,661 | 4/1947 | Staaf | 2/8 |
| 2,433,164 | 12/1947 | Shields | 2/8 |
| 2,459,021 | 1/1949 | Frommer | 88/41 |
| 3,325,824 | 6/1967 | Donegan | 2/8 |
| 3,572,931 | 3/1971 | Adler | 356/46 |
| 5,297,298 | 3/1994 | Salatka et al. | 2/452 |

FOREIGN PATENT DOCUMENTS

| | | | |
|---|---|---|---|
| 1289321 | 9/1972 | United Kingdom | 2/10 |

OTHER PUBLICATIONS

*Herrschners® Quality Needlecrafts Since 1899*, ©Copyright, Herrschners 1994; cover page, inside cover page and p. 46 (3 pp. total).

Instruction sheet on "Here is . . . 'The best you'll ever see' your SLIP-ON new 3-D Binocular Magnifier" made by Magna Sales Company of Shicago, Illinois 60618 (1 sheet-front and back) and two sheets containing six photographs of same. ©1994 Magna Sales.

Brochure published by Herrco Enterprises, Inc., Specialty Products of Baltimore, Maryland, entitled: "Telescopic Magnifiers", front and back (2 pgs. total).

"The Catalog of Magnifiers", published by C and E Optical, Inc. of Chicago, Illinois, front, back and inside covers, pp. 7 and 15, and price list from C and E Optical, Inc. dated Apr., 1993 (6 pgs. total).

"1993 Annual Reference Catalog For Optics, Science and Education", published by E. S. Edmund Scientific of Barrington, N.J.; ©1992 Edmund Scientific Co. vol. 13N1; front, back and inside covers and pp. 3, 101 and 186 (6 pgs. total).

Photocopy of box entitled: OptiVISOR Optical Glass Binocular Magnifier® made by Donegan Optical Company, Inc. (2 pgs. total) (See above U.S. Pat. No. 3,325,824).

6 photographs of black headband magnifier (no date but prior art) (2 pgs. total).

5 photographs of pink plastic "Canyon Ranch®" visor by 3-D Activewear, Inc., U.S. patent pending (2 pgs. total) (no date but prior art).

Lyondell Polymers Polypropylene Technical Data Sheet PP 51S12A dated Mar. 1991.

Brochure entitled: How To Get The Most From Your OptiVISOR!, published by Donegan Optical Company, Rev. Jan. 1991; front and back (2 pgs. total).

*Primary Examiner*—Diana Biefeld
*Attorney, Agent, or Firm*—Pravel, Hewitt, Kimball & Krieger

[57] ABSTRACT

A headband magnifier comprises a one-piece polypropylene headband having a front portion, a back portion and two opposed sides where the back portion is disengageable so that the headband is movable between an at rest position and a compression position for the headband to provide a compressive force. This headband compressive force provides a comfortable tension for all head sizes. The headband magnifier further provides a flexible holding member having a continuous groove that facilitates interchangeability of lenses.

15 Claims, 6 Drawing Sheets

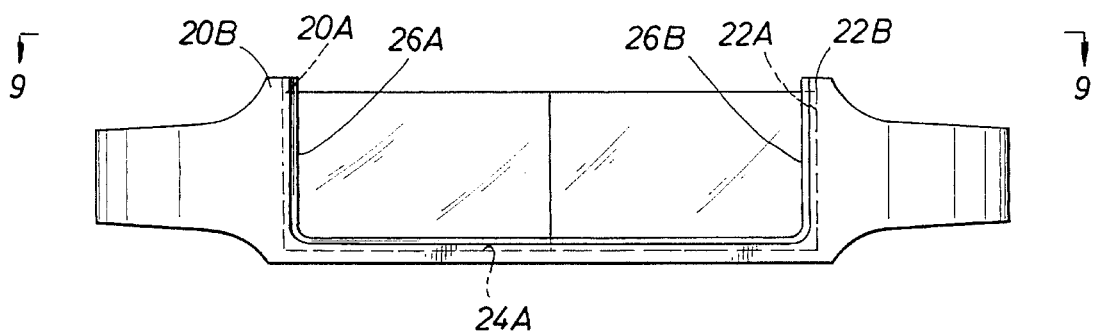
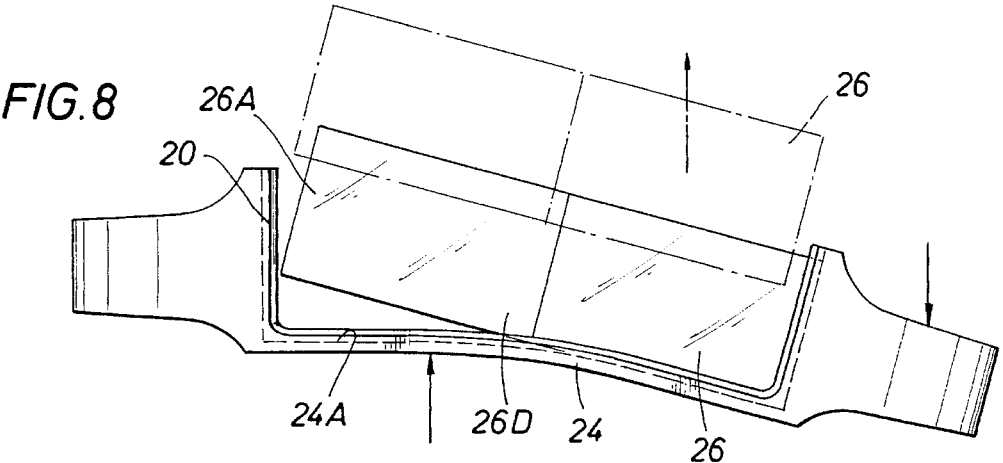
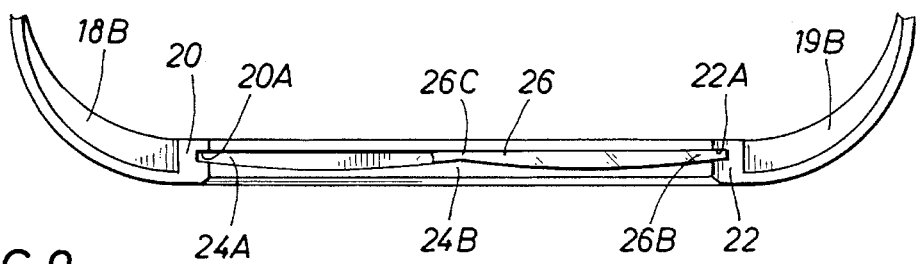
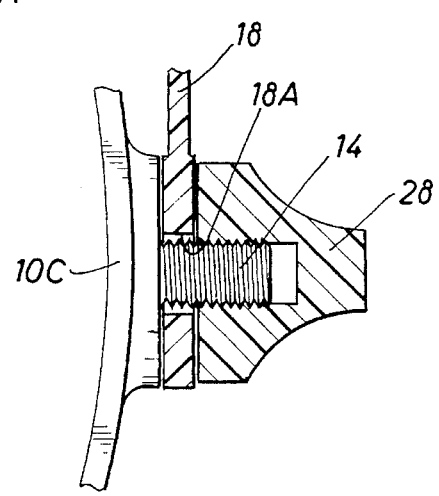

FIG.11
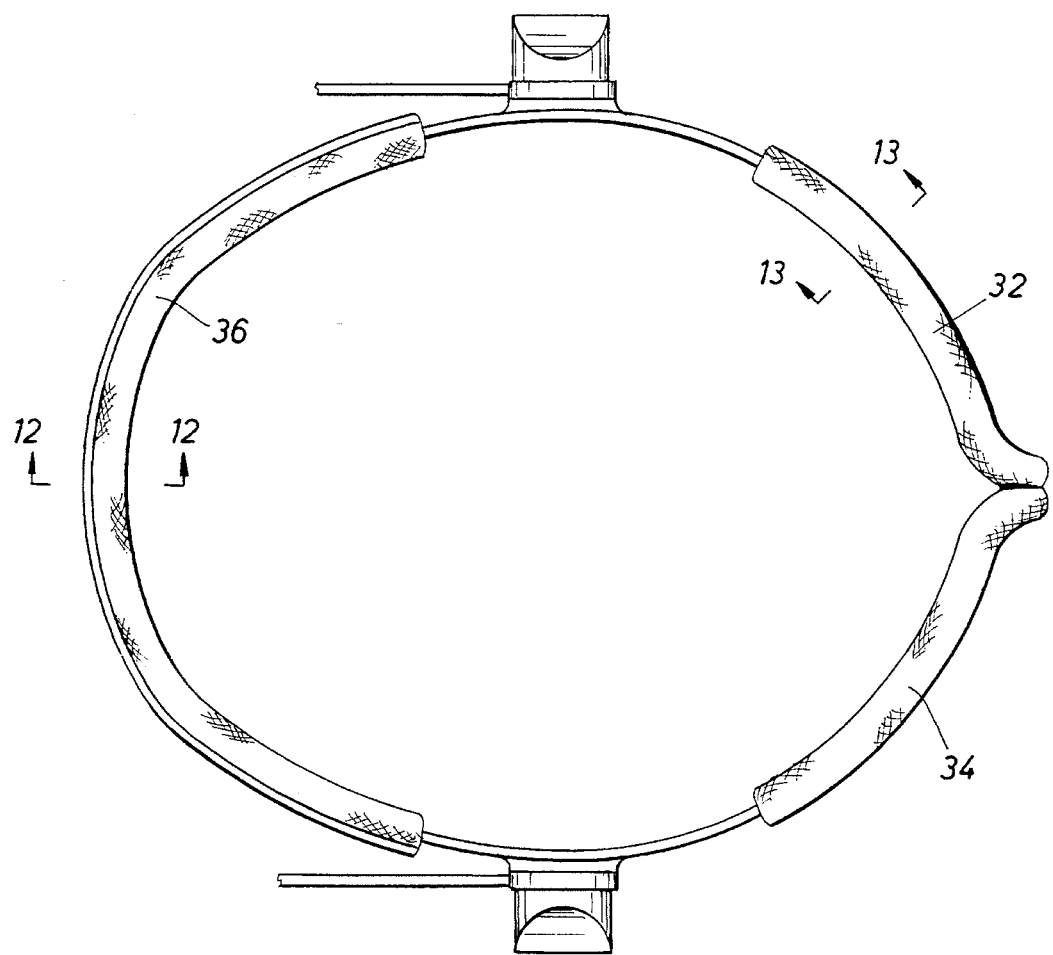
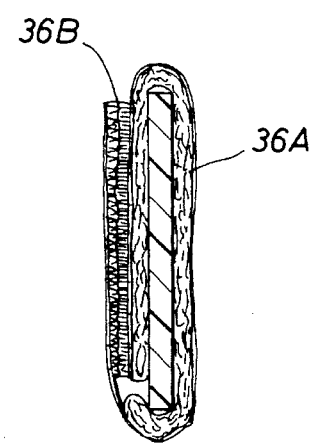
FIG.12
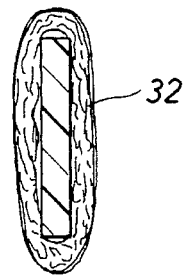
FIG.13

HEADBAND MAGNIFIER

This is a continuation-in-part of design application Ser. No. 29/014,845 filed Oct. 29, 1993 now U.S. Pat No. Des. 359,060.

FIELD OF THE INVENTION

This invention relates generally to an apparatus for magnifying an image and, more particularly, a compressive headband used to position a magnifying lens holding device that facilitates the interchangeability of lenses in the holding device.

BACKGROUND OF THE INVENTION

There are headbands in common use that are used to position a magnifying lens. U.S. Pat. No. 3,325,824 discloses a headband magnifier having an adjustable headband comprising a plastic strap. This headband magnifier is manufactured by Donegan Optical Company, Inc. of Lenexa, Kans. The headband is worn horizontally about a person's head substantially at forehead level. The plastic strap is received in a sleeve to conform the headband to a range of head sizes. An eye shade member can be moved in the line of sight of the wearer and a lens holder is mounted in the front wall of the eye shade member to receive a pair of magnifying lenses. This headband magnifier uses two screws received on each side of the rectangular shaped lenses for fastening the lens to the eye shade member. The eye shade is provided with a pair of rearwardly extending temple pieces which are pivoted respectively to the strap at opposite sides of the wearer's head by friction bolts so that the eye shade may be raised or lowered as desired.

Headband magnifiers have also been available with interchangeable lenses provided on eye shades members positioned from a headband, such as disclosed in Model 102-107 Visor Loupe sold by Herrco Enterprises, Inc. of Baltimore, Md. and the "Eschenbach" headband magnifier sold by C & E Optical, Inc. of Chicago, Ill.

Additionally, headband magnifiers have been configured so that the eye shade member can be worn over prescription eyeglasses such as the one sold by Edmond Scientific Company of Barrington, N.J.

Additionally, there is a headband magnifier available for positioning a magnifying lens that comprises a one-piece headband that completely encircles the user's head. The headband ends are adjustably secured by hook and pile to fit a number of sizes of heads. A U-shaped member includes two arms and a holding member that completely encircles the rectangular shaped lens member so as not to permit lens interchangeability.

Also, sun visors are available having a front shade portion and a back portion where the back portion is disengageable so that the headband is movable between an at rest position and a compression position for said visor to provide a compressive force for positioning on a number of different head sizes. Such a sun visor is sold by 3-D Activewear, Inc.

Headband magnifiers are used in daily activities such as reading classified ads, stock reports, newspapers, magazines, phonebooks, dictionaries and maps. Additionally, crafters use headband magnifiers for sewing, knitting, crocheting, embroidering, painting, stamp collecting, leatherworking or any craft where vision enhancement is desired. However, the available headband magnifiers completely encircle the user's head. This encircling strap is undesirable in that it would compress the user's hair in the back of the user's head. Therefore, it would be desirable to have a flexible headband that would create a comfortable tension for all head sizes without completely encircling the user's head. Such a hands-free flexible head mounted magnifier that could be worn with or without prescription glasses has long been desired.

Additionally, a headband magnifier that would facilitate the interchangeability of lenses so that one could change lens powers to provide the desired magnification of the image without requiring the use of screws or other additional fastening means and could be manufactured and assembled at a low cost has been desired.

SUMMARY OF THE INVENTION

According to the invention, a headband magnifier comprising a one-piece headband having a front portion, a back portion and two opposed sides where the back portion is disengageable so that the headband is movable between an at rest position and a compression position for the headband to provide a compressive force. This compressive force exerted by the headband provides a predetermined comfortable tension for all head sizes without completely encircling the user's head.

The improved headband magnifier further provides an inexpensive holding member that facilitates interchangeability of the lenses.

BRIEF DESCRIPTION OF THE DRAWING

The objects, advantages, and features of the invention will become more apparent by reference to the drawings which are appended hereto and wherein like numerals indicate like parts and wherein an illustrated embodiment of the invention is shown, of which:

FIG. 7 is an enlarged front view of the U-shaped member showing a continuous groove in dashed lines and showing the horizontal member of the holding member being in an at rest position;

FIG. 8 is a view similar to FIG. 7 with the horizontal member in a flexed position for facilitating removal of the lens;

FIG. 9 is a section view taken along line 9—9 of FIG. 7;

FIG. 10 is an enlarged section view of a threaded stud extending from the arm of the U-shaped member and a securing cap received on the stud;

FIG. 11 is an alternative embodiment of the present invention showing the headband in the at rest position and further showing an optional cushioning member received on the front portion of the headband;

FIG. 12 is a section view taken along line 12—12 of FIG. 11;

FIG. 13 is a section view taken along line 13—13 of FIG. 11;

DETAILED DESCRIPTION OF PREFERRED EMBODIMENT

The headband magnifier of the present invention is shown in the Figures. In particular, the preferred embodiment of the headband magnifier is shown in FIGS. 1–10 and the alternative embodiments of the headband magnifier are shown in FIGS. 10–19.

The preferred embodiment of the headband magnifier comprises a holding member that includes two opposed upright members and a single horizontal member thereby leaving one side open for removal of the lens to permit interchangeability of the lenses. The holding member of the alternative embodiment, as shown in FIGS. 14–19, includes two horizontal members and two upright numbers so as to completely encircle the lens, as will be discussed below in detail.

Figure 1:
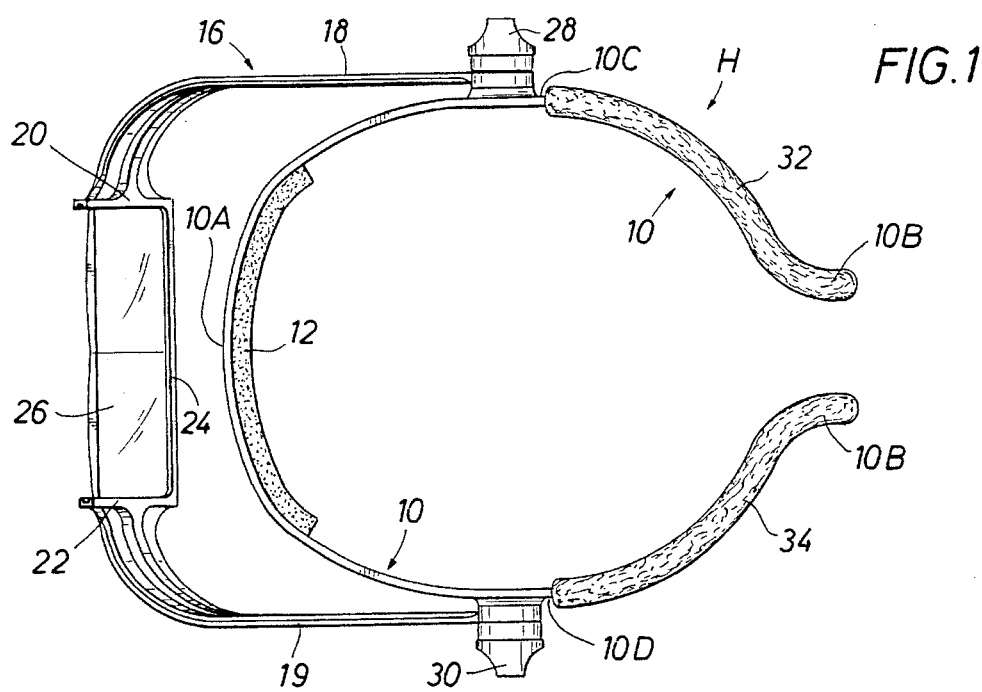
FIG. 1 is a plan view of the preferred embodiment of the headband magnifier of the present invention with the headband in the compression position.
Figure 4:
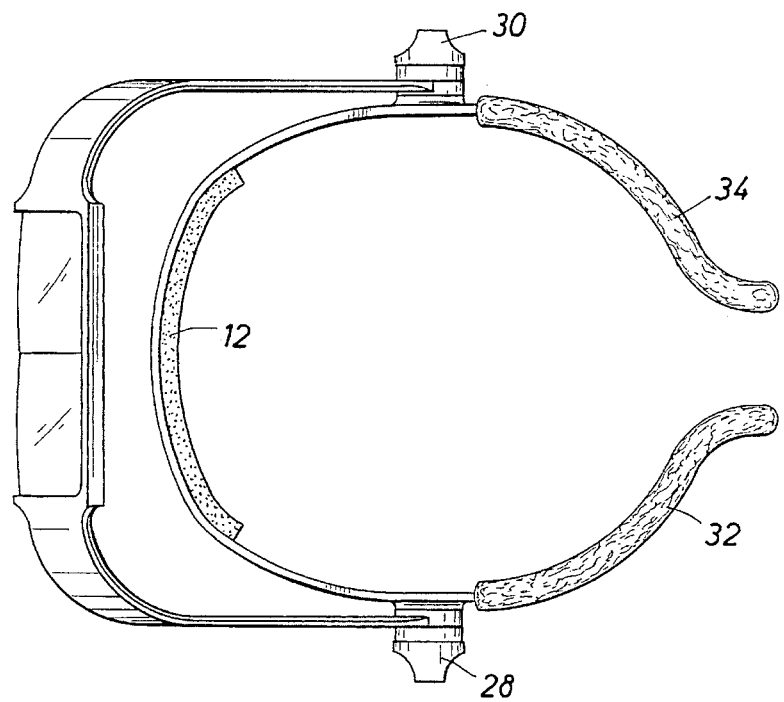
FIG. 4 is a bottom view of the headband magnifier shown in FIG. 1.
Figure 5:
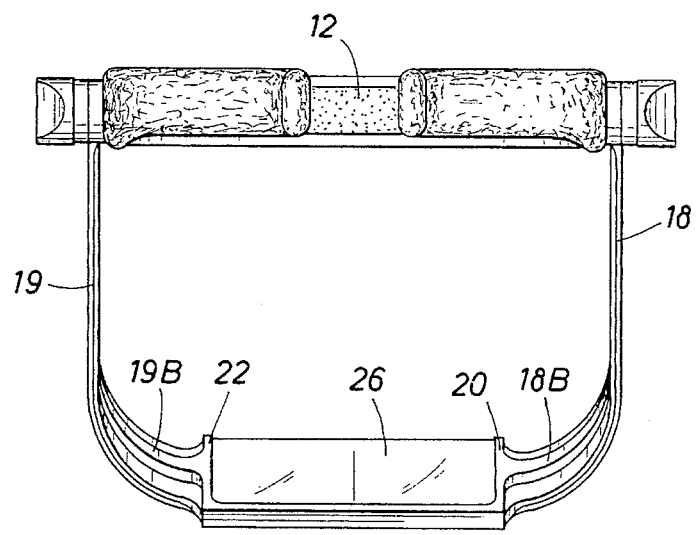
FIG. 5 is a rear view of the headband magnifier shown in FIG. 1.

However, each of the headband magnifiers of the present invention, generally designated as H for the preferred embodiment, and, H' for the alternative embodiment, includes a headband 10. The headband includes a front portion 10A, a back portion 10B and opposed sides 10C and 10D. The back portion 10B is disengageable so that the headband 10 is movable between an at rest position, as shown in FIG. 11, and a compression position, as best shown in FIGS. 1, 4 and 5, for the headband 10 to provide a compressive force, yet not be required to completely encircle the user's head. The headband 10 further includes a cushioning member 12 that extends radially inwardly substantially the distance of the headband front portion to engage the forehead of the user. As best shown in FIG. 10 a threaded stud 14 extends radially outwardly and is preferably molded into the headband side 10C. A similar threaded stud (not shown) is molded into and extends outwardly from side 10D.

Figure 2:
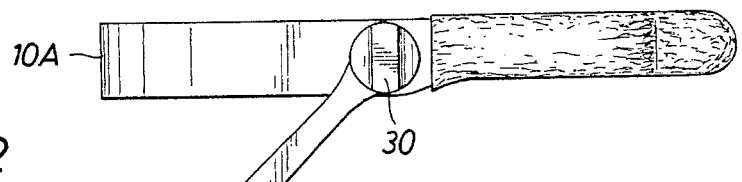
FIG. 2 is a side view of the present invention as shown in FIG. 1, the opposite side of the headband magnifier being a mirror image of FIG. 2.
Figure 3:
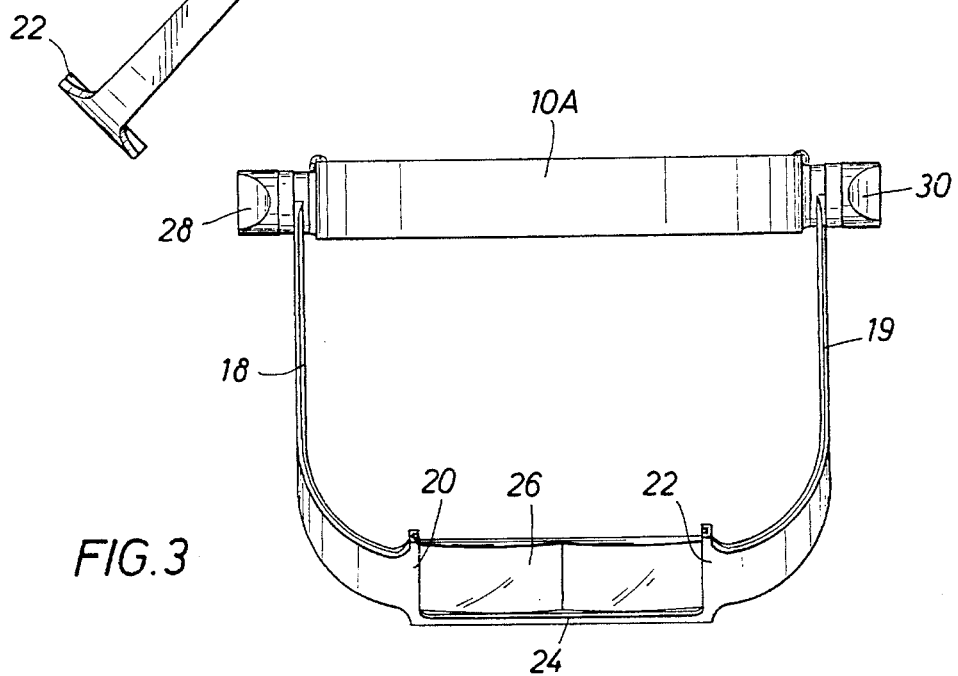
FIG. 3 is a front view of the headband magnifier shown in FIG. 1.

Turning now to FIG. 1, a U-shaped member, generally indicated at 16, comprises an arm 18 and an arm 19 and a holding member comprising uprights 20 and 22 and a horizontal member 24. A one piece lens 26 is positioned in the holding member, as will be discussed below in detail. The arm 18 of the U-shaped member includes a bore 18A that is received about stud 14 and a cap 28 having internal threads is received on stud 14 to provide a friction force on the arm 18 against the side 10C. A similar bore in arm 19 is received on the threaded stud extending radially outwardly from side 10D and a cap 30, similar in use to cap 28, is used to provide a friction force on arm 19 against side 10D. Of course, the friction force on the arms can be adjusted by tightening of the cap 28 and/or cap 30. Alternatively, to reduce cost, the radially outwardly extending studs could be non-threaded cylindrical studs (not shown) that would receive a conventional "PAL" self-threading nut (not shown), instead of caps 28, 30. As best seen in FIGS. 1, 11 and 13, the rear portion 10B and a portion of the opposed sides 10C and 10D are preferably covered with cushioning members 32 and 34, respectively. Alternatively, these cushioning members 32 and 34 could be removed so that the rear portion 10B would directly engage the user's head. If the members 32 and 34 were removed, the rear portion would have the same thickness of front portion 10A of the headband and a similar but reduced configuration of the members 32 and 34, as shown in FIGS. 1 and 2.

As best seen in FIG. 5 of the preferred embodiment each of the arms 18 and 19 includes respective stiffening members 18B and 19B. These stiffening members provide structural integrity to the arms and are preferably integrally molded with the upright members 20 and 22, respectively.

Turning now to FIG. 7, a continuous groove in the holding member is shown by dashed lines. As best shown in FIG. 9, the upright member groove 20A and upright member groove 22A provides a friction fit with a portion of the sides 26A and 26B, respectively, of lens 26. The horizontal member groove 24A is also sized so as to provide a friction fit with the bottom of lens 26. Particularly, a central portion 24B of horizontal member 24 is sized so as to provide a friction fit with the portion of the reduced portion 26C of the lens 26, as best shown in FIG. 9. It will be noted that the upright members 20 and 22 include an extended portions 20B and 22B, respectively, so that upon placing the headband magnifier on a flat surface, the extended portions 20B and 22B reduce the possibility of damage to the lens 26. Therefore, the grooves 20A, 24A and 22A provide a continuous groove for receiving the portions 26A, 26C, 26D and 26B of the lens 26.

The horizontal portion 24, the U-shaped member and headband 10 are preferably fabricated from polypropylene. A preferred polypropylene PP 51S12A (Homopolymer) is sold by Lyondell Polymers of Houston, Tex., a subsidiary of Lyondell Petrochemical Company. This polypropylene has a tensile yield strength of 4,700 psi, tensile ultimate elongation of >100%, a tensile modulus of 210,000 psi, flexural modulus of 200,000 psi, deflection temperature of 225° F. and a Rockwell hardness of 95R.

Turning now to FIG. 11, an alternative cushioning member for the front portion of the headband 10 is shown. The cushion member 36 includes a cushion portion 36A on the radially inward side of the front portion to engage the forehead of the user. On the opposed side of the front portion is a hook and pile fastener 36B to provide easy engagement and disengagement of the cushioning member 36 for cleaning, replacement or for non-use as desired by the user. Another alternative for cushioning the headband front portion 10A would be to provide a continuous tube of cushioning material (not shown) over the front portion 10A. The continuous tube of cushioning material could be elastic enough to pass over the stud 14 or could pass over the stud 14 without being stretched and could be heat treated to shrink in engagement with the front portion 10A.

FIGS. 14–19 disclose an alternative embodiment of the present invention. The headband member 10 is similar to the preferred embodiment, as are the cushion members 32, 34 and 12. The U-shaped member 16' differs from the preferred embodiment in that an additional horizontal member 38 is provided so that the holding member completely encircle the lens 26. This additional horizontal member 38 could be molded with the uprights in which case the lens would not be interchangeable. Alternatively, the additional horizontal member 38 could be removably received in the grooves 20A, 22A adjacent extended portions 20B and 22B, respectively, with conventional means, such as an interference fit or a pop in fit. Upon removal of the additional horizontal member 38, the head magnifier of FIGS. 14–19 could operate as discussed for the preferred embodiment of FIGS. 1–9. As another alternative, the back or front side of the holding member shown in FIGS. 14–19, preferably the back, could be removably secured to the holding member (not shown). Upon removal of the back side, the lens 26 could be accessible for assembly, replacement or interchangeability of the lens.

Use and Operation

Figure 6:
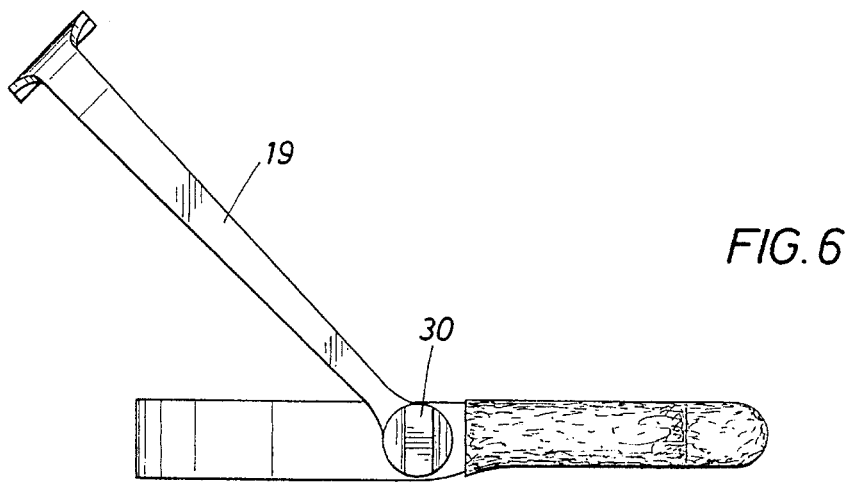
FIG. 6 is a view similar to FIG. 2 with the U-shaped member for holding the lens being moved to an up position.
Figure 14:
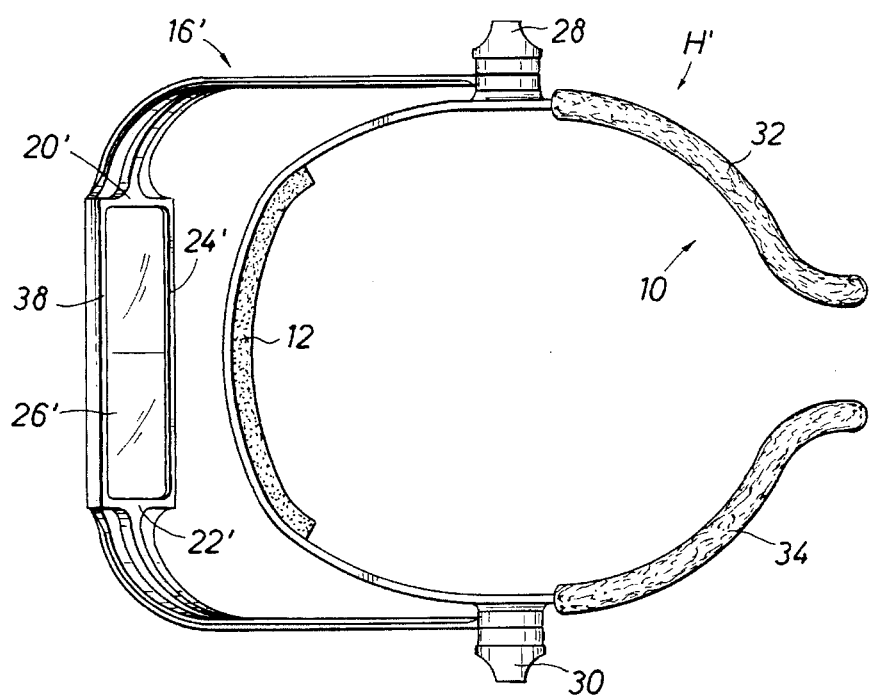
FIG. 14 is a plan view of an alternative embodiment of the headband magnifier of the present invention with the headband in the compression position.
Figure 15:
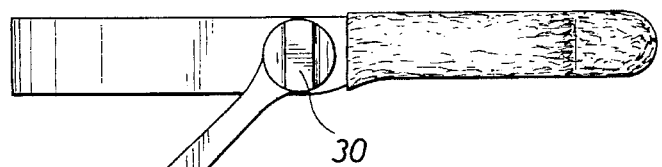
FIG. 15 is a side view of the present invention as shown in FIG. 14, the opposite side of the headband magnifier being a mirror image of FIG. 15.
Figure 16:
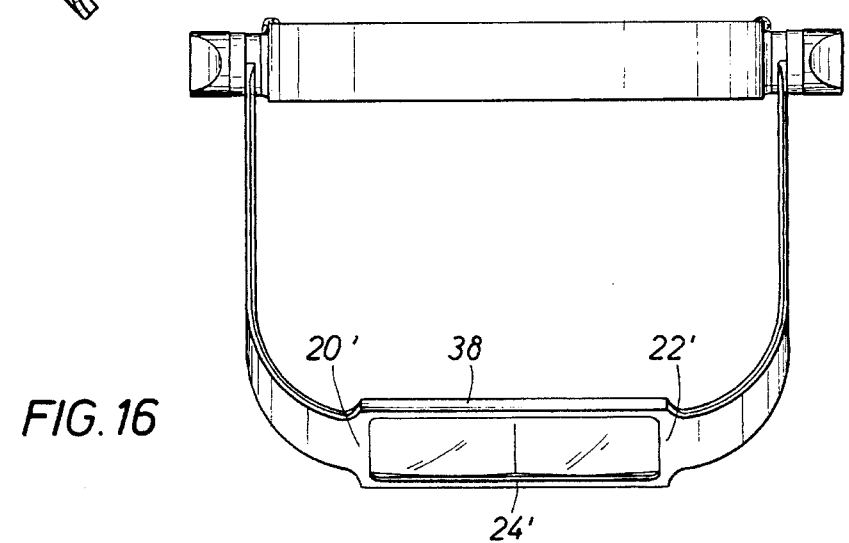
FIG. 16 is a front view of the headband magnifier shown in FIG. 14.
Figure 17:
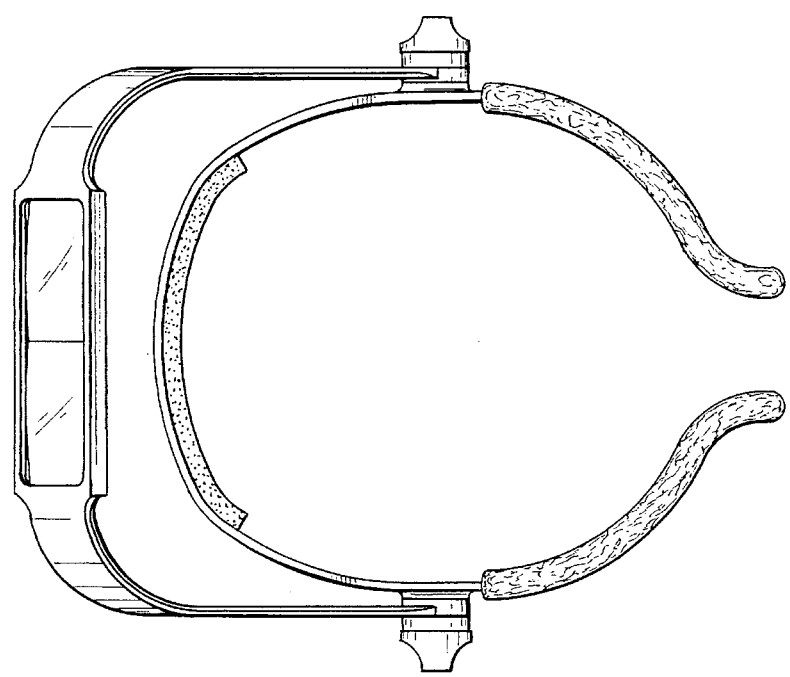
FIG. 17 is a bottom view of the headband magnifier shown in FIG. 14.
Figure 18:
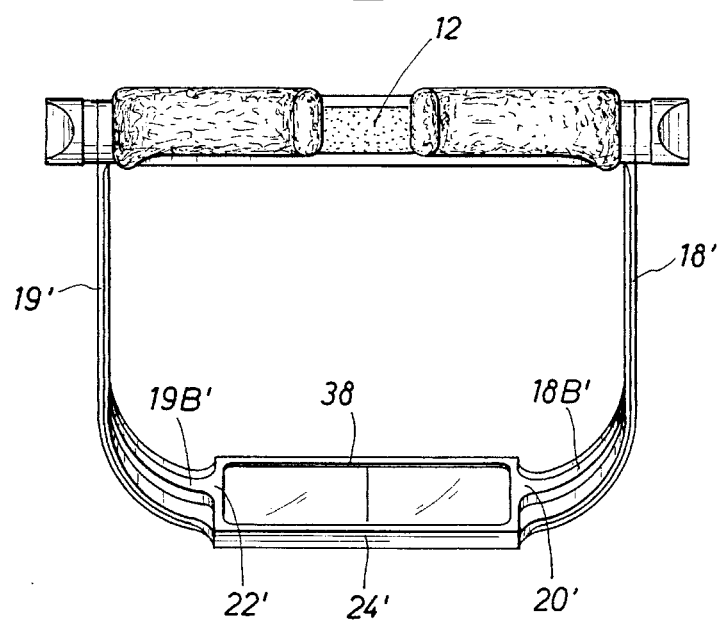
FIG. 18 is a rear view of the headband magnifier shown in FIG. 14.
Figure 19:
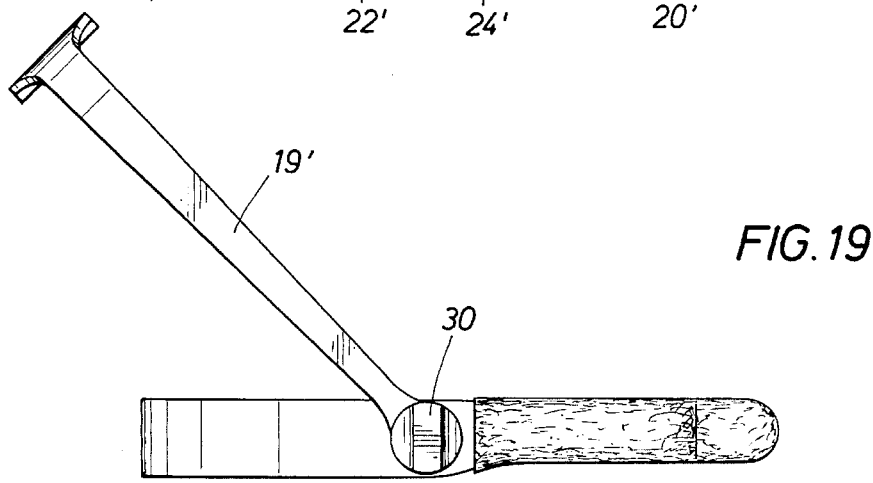
FIG. 19 is a view similar to FIG. 15 with the U-shaped member for holding the lens being moved to an up position.

When the user selects the desired headband magnifier, the rear portions are graped and spread apart so as to move the headband from at rest position, shown in FIG. 11, where the ends engage each other, to the compressive position to provide a compressive force, such as shown in FIGS. 1, 4, 5, 14, 17 and 18. In this disengaged position, the ends of the headband rear portion are moved generally rearward from the user's temples and properly positioned to provide a comfortable tension on the user's head. This predetermined tension force is designed to support the selected U-shaped member and lens. The caps 28 and 30 can then be adjusted, if necessary, to maintain the positioning of the U-shaped member 16 in the line of sight of the user. When desired, the U-shaped member 16 can be moved from a line of sight position, such as shown in FIGS. 2 and 15, to an up position, as shown in FIGS. 6 and 19, out of the line of sight and out of the way of the user. It also should be appreciated that all the embodiments of the invention can be used in combination with conventional prescription glasses.

If the user desires to change the lens, the user would remove the headband and grasp the front end of arms 18, 19 of the U-shaped member 16. The user would then apply a force with their hands, such as shown in FIG. 8, to one of the arms while maintaining the other arm in the initial position so that the horizontal member 24 is flexed. Upon moving the horizontal member 24 to the flexed position, as shown in FIG. 8, one side of the lens 26A is spaced apart from its respective upright member 20 to facilitate removal of the lens upwardly, as shown in dashed lines in FIG. 8. Upon removal of the force to one of the arms, the U-shaped member returns to its at rest position, such as shown in FIG. 7, whereupon another similar length and height lens, with a desired power, can be inserted into the grooves 20A, 24A and 22A of the holding member to provide a friction fit of the holding member with the lens 26. The friction fit of the lens within the holding member is designed so that even if the headband magnifier were turned upside down, so that the horizontal member 24 was above the lens, and the headband magnifier was shaken, the lens would still remain in position, as shown in FIG. 7. Alternatively, referring to FIG. 7, a hub (not shown) could be molded into each groove 20A, 22A above the top of lens sides 26A and 26B, respectively. These nubs would be sized to allow interchangeability of the lens, as shown in FIG. 8, but the nubs would provide interference if the lens 26 were moved upwardly when the horizontal member 24 was not in the flexed position.

Though only one lens is shown, the embodiments of FIGS. 1–9 are designed to be removable and interchangeable with different powers of lens. Preferably, there would be a 2.5X power lens and a 4.0X power lens, though any power of lenses could be used as desired by the user. Preferably, the lens is 3.465 inches in length and 1.550 inches in height. Of course, the thickness of the lens would depend on the power of the lens used. The lenses are preferably not hard coated and are fabricated from an ultraviolet acrylic. One such preferred lens is Model No. V825-UVA sold by AOtec, Inc. of Southbridge, Mass.

The foregoing disclosure and description of the invention are illustrative and explanatory thereof, and various changes in the size, shape, and materials, as well as in the details of the illustrated construction may be made without departing from the spirit of the invention.

We claim:

1. Apparatus for magnifying an image, comprising, a one-piece headband having a front portion, a back portion and two opposed sides, said headband being movable between an at rest position and a compression position wherein said headband provides a compressive force while said headband back portion is disengaged, a U-shaped member having two arms and a holding member, one end of each of said arms being movably positioned on said opposed sides of said headband and the other end of each of said arms supporting said holding member, said holding member comprising opposed upright members supported by said arms, said holding member further comprising a flexible horizontal member to interengage said opposed upright members, and a magnifying lens positioned in said holding member, said horizontal member being movable between an at rest position and a flexed position for facilitating removal of said lens.

2. Apparatus of claim 1 wherein said upright members and said horizontal member have a continuous groove sized to receive a portion of said magnifying lens.

3. Apparatus of claim 2 wherein said continuous groove provides a friction fit of said holding member with a portion of said magnifying lens.

4. Apparatus for magnifying an image, comprising, a one-piece headband having a front portion, a back portion and two opposed sides, said headband being movable between an at rest position and a compression position wherein said headband provides a compressive force while said headband back portion is disengaged, a U-shaped member having two arms and a holding member, one end of each of said arms being movably positioned on said opposed sides of said headband and the other end of each of said arms supporting said holding member said holding member comprising opposed upright members supported by said arms, and a magnifying lens positioned in said holding member, said upright members having grooves sized to receive a portion of said magnifying lens, said magnifying lens having a reduced diameter portion and said horizontal member groove being sized to provide a friction fit of said holding member with a portion of said lens reduced diameter portion.

5. Apparatus for magnifying an image, comprising, a one-piece headband having a front portion, a back portion and two opposed sides, said headband being movable between an at rest position and a compression position wherein said headband provides a compressive force while said headband back portion is disengaged, a U-shaped member having two arms and a holding member, said holding member fabricated from polypropylene, one end of each of said arms being movably positioned on said opposed sides of said headband and the other end of each of said arms supporting said holding member, and a magnifying lens positioned in said holding member.

6. Apparatus for magnifying an image, comprising, a headband having a front portion, a back portion and two opposed sides, a U-shaped member having two arms and a holding member, one end of each of said arms being movably positioned on said opposed sides of said headband and the other end of each of said arms supporting said holding member, a magnifying lens removably positioned in said holding member, and said holding member comprises opposed upright members supported by said arms and a flexible horizontal member to interengage said opposed upright members, said horizontal member movable between an at rest position and a flexed position for facilitating removal of said lens.

7. Apparatus of claim 6 further comprising threaded studs extending radially outwardly on said opposed sides of said headband and said one end of each of said arms having bores therein, said studs being received in said arm bores to movably position said U-shaped member on said headband.

8. Apparatus of claim 6 wherein said upright members and said horizontal member have a continuous groove sized to receive a portion of said magnifying lens.

9. Apparatus of claim 8 wherein said continuous groove provides a friction fit of said holding member with a portion of said magnifying lens.

10. Apparatus of claim 8 wherein said magnifying lens has a reduced diameter portion and said horizontal member groove is sized to provide a friction fit of said holding member with a portion of said lens reduced diameter portion.

11. Apparatus for magnifying an image, comprising, a one-piece headband having a front portion, a back portion and two opposed sides, said back portion being disengageable so that said headband is movable between an at rest position and a compression position for said headband to provide a compressive force, a U-shaped member having two arms and a holding member, one end of each of said arms being movably positioned on said opposed sides of said headband and the other end of each of said arms supporting said holding member, a magnifying lens having opposed sides and removably positioned in said holding member, and said holding member comprises opposed upright members supported by said arms and a flexible horizontal member to interengage said opposed upright members, said upright members and said horizontal member having a continuous groove sized to receive a portion of said magnifying lens, said horizontal member movable between an at rest position and a flexed position whereby upon moving said horizontal member to the flexed position a portion of one of the opposed sides of the magnifying lens is spaced apart from one of said upright members to facilitate removal of said lens.

12. Apparatus of claim 11 wherein said magnifying lens has a reduced diameter portion and said horizontal member groove is sized to provide a friction fit of said holding member with a portion of said lens reduced diameter portion.

13. Apparatus for magnifying an image, comprising, a one-piece headband having a front portion, a back portion and two opposed sides, said back portion being disengageable so that said headband is movable between an at rest position and a compression position for said headband to provide a compressive force, a U-shaped member having two arms and a polypropylene holding member, one end of each of said arms being movably positioned on said opposed sides of said headband and the other end of each of said arms supporting said holding member, and a magnifying lens positioned in said holding member.

14. Apparatus of claim 13 wherein said holding member comprises a flexible horizontal member, said horizontal member movable between an at rest position and a flexed position for facilitating removal of said lens.

15. Apparatus of claim 13 wherein said holding member comprises opposed upright members supported by said arms.

\* \* \* \* \*